United States Patent [19]
Lichtenstein

[11] 4,392,856
[45] Jul. 12, 1983

[54] VASCULAR PUNCTURE STABILIZER FITTING FOR FACILITATING WITHDRAWAL

[75] Inventor: Joseph Lichtenstein, Colonia, N.J.

[73] Assignee: Whitman Medical Corporation, Clark, N.J.

[21] Appl. No.: 314,481

[22] Filed: Oct. 23, 1981

[51] Int. Cl.³ .............................................. A61M 5/00
[52] U.S. Cl. .................................................... 604/177
[58] Field of Search ..................... 128/214, 214.4, 133, 128/221, DIG. 26

[56] References Cited

U.S. PATENT DOCUMENTS

| | | | |
|---|---|---|---|
| 3,973,565 | 8/1976 | Steer | 128/214.4 |
| 4,129,128 | 12/1978 | McFarlane | 128/DIG. 26 X |
| 4,324,236 | 4/1982 | Gordon et al. | 128/DIG. 26 X |

*Primary Examiner*—Stephen C. Pellegrino
*Attorney, Agent, or Firm*—Holman & Stern

[57] ABSTRACT

A fitting for inserting a needle or catheter into a blood vessel and for positionally stabilizing the inserted needle or catheter in situ includes separate needle holder and stabilizer elements. A retainer member is secured at its proximal end to the holder and extends in spaced relation along the holder to a distal end. The stabilizer has a bi-wing shape with a slot contoured to receive the retainer member in longitudinally slidable relation at a location below a holder supporting region on the top surface of the stabilizer. The wings can be flexed upward and toward one another to positively grip the holder for insertion of the needle or catheter. When unflexed, the stabilizer slot constrains the retainer element which in turn holds the stabilizer in the space between the retainer and the holder. Removal of the needle is achieved by withdrawing the retainer longitudinally from the stabilizer slot.

16 Claims, 6 Drawing Figures

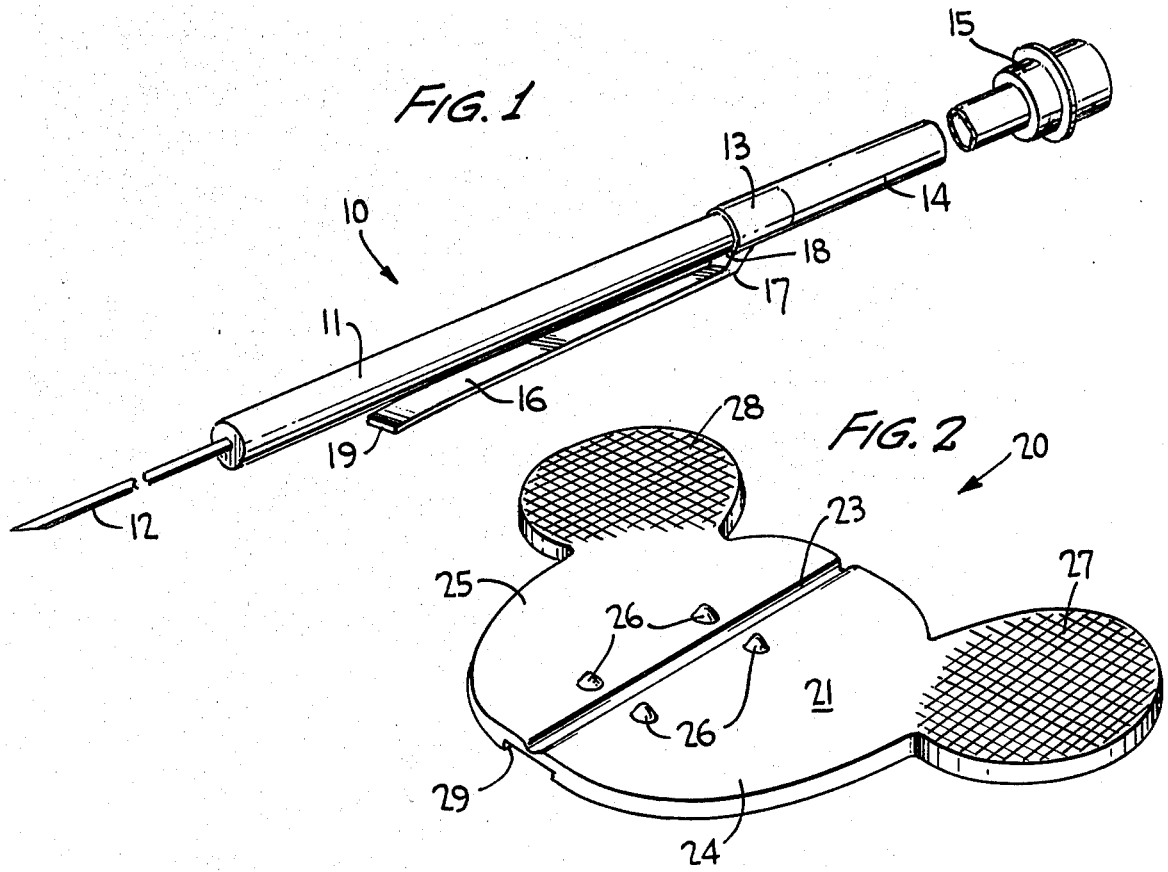
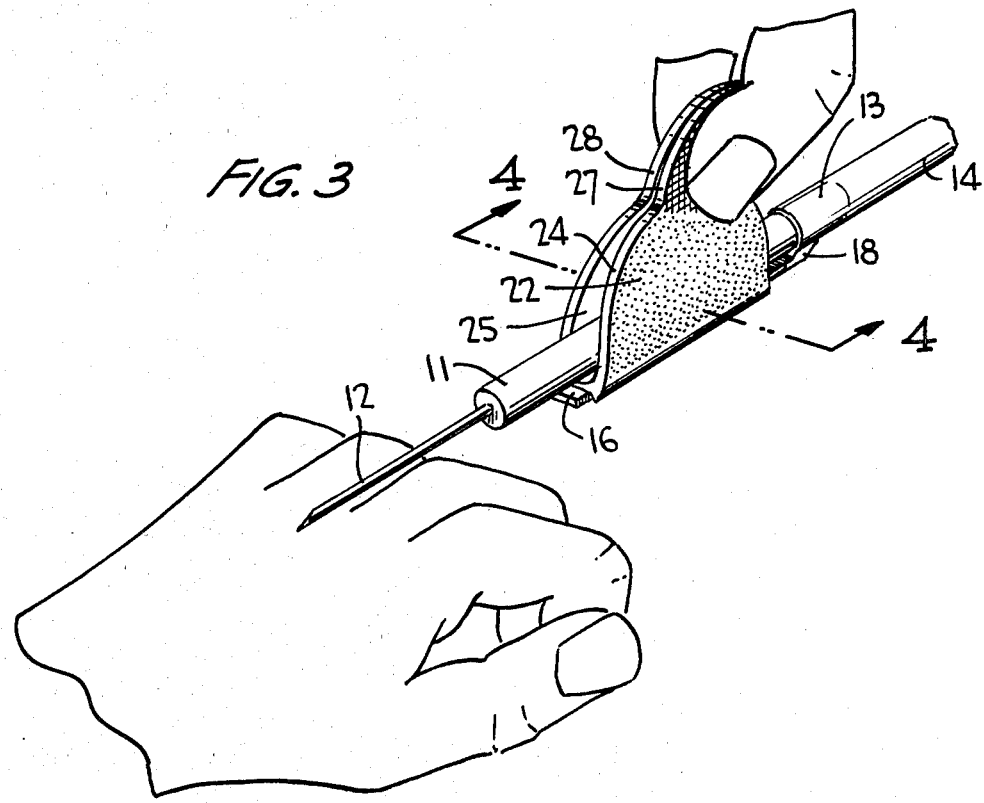

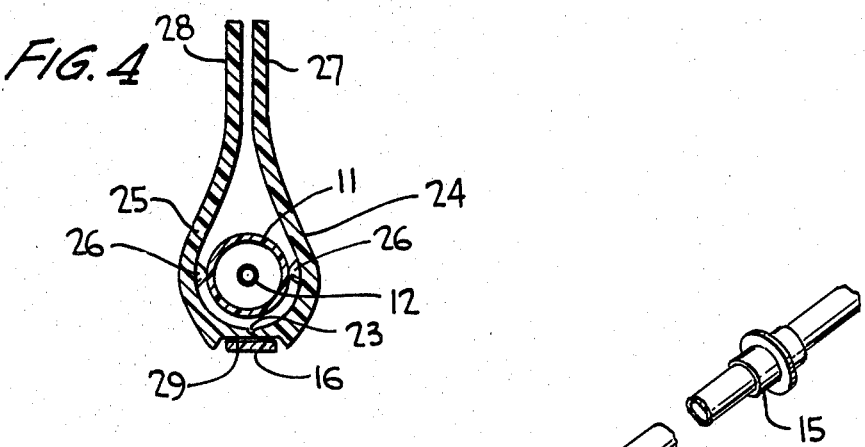
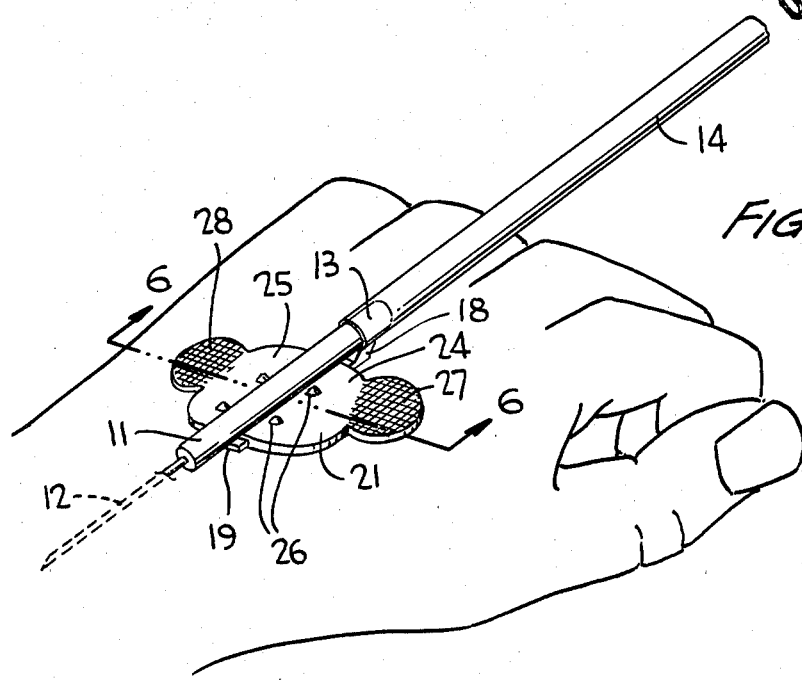
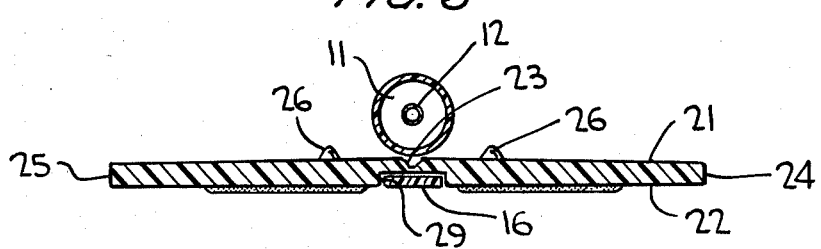

VASCULAR PUNCTURE STABILIZER FITTING FOR FACILITATING WITHDRAWAL

TECHNICAL FIELD

The present invention relates to fittings for inserting a needle or catheter into a blood vessel and for positionally stabilizing the inserted needle or catheter in situ. More particularly, the present invention relates to improvements in such fittings whereby the needle or catheter can be withdrawn from the blood vessel with minimum risk of blood vessel damage.

BACKGROUND OF THE INVENTION

Vascular punctures can be made in many areas of the body by means of a hollow needle or combined catheter and stylet, the needle or catheter (after withdrawal of the associated stylet) remaining attached to the patient for connection to a source of infusion liquid. It is necessary in such procedures to positionally stabilize the needle or catheter in relation to the punctured blood vessel to prevent movement of the needle or catheter. Such movement tends to work the needle or catheter loose or to produce undesirable additional blood vessel punctures, thereby leading to a potential source of infection or irritation to the patient at the point of insertion of the needle or catheter. There are numerous small vein needle infusion sets disclosed in the prior art; for example, reference is made to U.S. patent application Ser. No. 99,926, filed Dec. 03, 1979 by Marvin Gordon and Joseph Lichtenstein and entitled "Fitting For Use In Performing A Vascular Puncture." These generally include a molded needle holder and one or more wings which are flexible about the holder. For insertion of the needle the wings are flexed toward one another and firmly grasped by the nurse or doctor as the needle is inserted into the vein. The wings are then released to provide positional stability on the patient's body and tape is applied to hold the entire system in place. The unit described in the aforementioned U.S. patent application Ser. No. 99,926 provides a solution for minimizing the danger of lateral shifting of the needle and resulting piercing of the vein during the insertion phase. However, there still remains the danger of piercing the vein during needle withdrawal.

SUMMARY OF THE INVENTION

It is therefore an object of the present invention to provide a fitting for a blood vessel-entering element which permits safe insertion, safe positional stabilization in situ, and safe withdrawal of the element. It is a further object of the present invention to provide a needle or catheter positional stabilization fitting which permits the needle or catheter to be safely removed with minimal danger of inadvertent piercing of a blood vessel.

In accordance with the present invention, a positional stabilization fitting includes a stabilizer member and a holder for a needle or catheter. During insertion, the stabilizer is flexible to permit the holder to be grasped firmly so as to preclude movement of the holder relative to the stabilizer element in any direction. After insertion, the stabilizer retains the holder in place by precluding relative movement between the stabilizer and the holder in any dimension except longitudinally of the holder. Since longitudinal movement of the holder relative to the stabilizer is unimpeded, after the infusion procedure, the needle can be withdrawn longitudinally from the stabilizer which precludes lateral movement of the holder during the withdrawal process and thereby prevents inadvertent piercing of the vein during the withdrawal. In the preferred embodiment, the holder is an elongate member having a retainer element as an integral part thereof. The retainer element has a proximal end secured to the elongate holder section and a distal free end spaced from the elongate holder section. The stabilizer includes at least one wing and preferably two and is flexible so that when the elongate holder section extends along the top surface of the stabilizer, the wings can be flexed upward toward one another to permit the holder to be firmly grasped for purposes of needle insertion. A slot is defined in the stabilizer to receive the retainer member in longitudinally slidable relation. This slot may be defined as an open channel in the bottom surface of the stabilizer or as a closed slot extending in the stabilizer body. In any case, the slot and retainer section extend beneath the elongate holder with the slot precluding relative movement of the holder and stabilizer except in the longitudinal direction. After insertion, the wings are released so as to rest with their bottom surfaces against the patient's skin. In the preferred embodiment, the bottom surface of the wings is coated with adhesive to effect initial stabilization. The entire system is then taped in place, as is conventional, until the infusion procedure is complete. In order to remove the needle from the vein, the tape is first removed and the holder is pulled longitudinally rearward. Engagement of the retainer member by the slot prevents lateral movement of the needle during withdrawal, the retainer member being engaged in at least a portion of the slot until the entire needle has been removed from the vascular insertion point.

BRIEF DESCRIPTION OF THE DRAWINGS

The above and still further objects, features, and advantages of the present invention will become apparent upon consideration of the following detailed description of one specific embodiment thereof, especially when taken in conjunction with the accompanying drawings, wherein:

FIG. 1 is a view in perspective of the holder portion of the fitting of the present invention;

FIG. 2 is a view in perspective view of the stabilizer member portion of the fitting of the present invention;

FIG. 3 is a view in perspective illustrating the fitting of the present invention in a position whereby it can be inserted into a blood vessel;

FIG. 4 is a view in section taken along lines 4—4 of FIG. 3;

FIG. 5 is a view in perspective showing the fitting of the present invention stabilized positionally after the needle has been inserted into a blood vessel; and FIG. 6 is a view in cross-section taken along lines 6—6 of FIG. 5.

DESCRIPTION OF THE PREFERRED EMBODIMENT

Referring specifically to FIG. 1 of the accompanying drawing, a needle support 10 includes a generally cylindrical holder member 11 securely supporting a needle 12 which projects co-axially from the forward end of member 11. Holder member 11 may be molded about the contained rearward end of needle 12 or may be otherwise secured thereto in any conventional manner so as to preclude mutual axial displacement of needle 12 and holder 11 during insertion of the needle into a blood vessel in the manner described herein. Holder member 11 is hollow inside, as is needle 12, so that infusion fluid supplied to the interior of member 11 can be delivered through needle 12 to a blood vessel. In order to receive such infusion fluid, the rearward end of member 11 is provided with a socket 13 to which one end of a supply tube 14 attaches. A connector 15, secured to the other end of tube 14, delivers the infusion fluid to the tube and holder.

A retainer member 16, preferably formed integrally with holder member 11, is in the form of a flat paddle-like stem having a proximal end 18 and a distal end 19. The transverse cross-section of retainer 16 is generally rectangular. The proximal end 18 of retainer member 16 is secured to holder member 11 proximate socket 13 at the rearward end of member 11. Proximal end 18 of retainer 16 extends a short distance away from holder member 11 at which point the retainer 16 bends at 17 so as to extend in a forward direction along side and in spaced relation with holder 11. The space between retainer 16 and holder member 11 may be approximately characterized as a U-shaped channel with bend 17 constituting the base of the U. Retainer 16 may extend parallel to holder 11; however, in the preferred illustrated embodiment, retainer 16 is angled slightly with respect to the longitudinal axis of holder 11. This angle, on the order of 5°, causes retainer 16 to converge slightly so that distal end 19 is somewhat closer to the holder 11 than is bend 17. The transverse spacing between the retainer 16 and holder 11 is important as described hereinbelow. In the preferred embodiment, retainer 16 is somewhat flexible so that a body disposed between the retainer and holder 11 is resiliently urged against the holder by the retainer. Holder 11 and retainer 16 are preferably molded together as one piece of thermoplastic and is sufficiently rigid to preclude significant transverse bending.

Referring to FIG. 2, a positional stabilization member 20 has a top surface 21 and bottom surface 22 (shown in FIG. 3, but not in FIG. 2). A holder support region 23 is defined in top surface 21 as a longitudinally-extending channel having a V-shaped cross-section. This groove serves as a "living hinge" which permits stabilization member 20 to be flexed upwardly about region 23. A pair of wing-like members 24,25 normally extend transversely from opposite sides of the region 23 and can be brought into partial contact with one another when flexed upwardly about region 23. Wing-like members 24,25 include respective co-planar projections 27,28 which extend outwardly and rearwardly relative to support region 23. A plurality of small nipple-like protuberances of generally truncated spherical shape are defined in rows extending along side support region 23 on the top surface 21.

Bottom surface 22 of stabilization member 20 has a slot 29, in the form of an open channel of generally rectangular transverse cross-section, extending longitudinally beneath support region 23. The transverse cross-section of slot 29 is configured to match that of retainer 16 so that the latter can slide longitudinally in the slot and be precluded from transverse movement within the slot. Portions of bottom surface 22 are provided with a suitable adhesive coating, as is conventional for such applications, so that the bottom surface can adhere to a patient's skin for initial positional stabilization after insertion of needle 12 into a blood vessel. The adhesive coating is not applied in slot 29 and is also not applied to the region of projections 27,28. Suitable release paper (not shown) is applied over the adhesive coating, as is conventional, to protect the coating prior to utilization of the unit.

Referring to FIGS. 3 and 4, when the unit is ready for insertion of the needle into a patient's blood vessel, the quick release paper (not shown) is removed from the adhesive-coated areas on bottom surface 22. Stabilization member 20 is inserted in the U-shaped channel between retainer 16 and holder member 11. Specifically, stabilization member 20 is positioned so that channel 29 receives retainer 16 and holder member 11 is positioned along support region 23. In this position, the forward end of holder member 11, along with needle 12, extends forwardly of the forward end of stabilization member 20. Wings 24,25 are flexed upwardly toward one another around holder member 11 by appropriately grasping the projections 27,28 which are not coated with adhesive. The wing-like members tightly engage holder 11 therebetween so as to preclude relative motion of any kind between the holder 11 and the stabilization member 20. This tight grasping of holder member 11 is enhanced by nipple-like protuberances 26 which, as best seen in FIG. 4, bear firmly against holder 11. With holder 11 thusly grasped, the needle 12 is inserted into the patient's blood vessel. After insertion, the wing-like members 24, 25 are released to their normal flat positions so that the adhesive coated regions on bottom surface 22 contact the patient's skin and thereby provide initial positional stabilization of the unit. In this position, as best illustrated in FIGS. 5 and 6, the wing-like members 24, 25 extend substantially transversely of the longitudinal axis of holder 11 and retainer 16 is retained between channel 29 and the patient's skin. With retainer 16 so constrained, attached holder 11 is constrained against any movement transverse to its longitudinal axis. In other words, holder 11 is constrained against roll, pitch, and yaw. The only possible movement of holder 11 at this time is rearward longitudinally of its axis. In order to preclude such longitudinal movement, surgical tape is placed over the stabilized unit to secure the unit to the patient's skin in the standard manner.

In order to withdraw the needle from the patient's blood vessel, the surgical tape is first removed. Holder 11 is then grasped and pulled rearwardly in an axial direction. Since channel 29 constrains retainer 16 against any lateral movement, needle 12 may be withdrawn without any chance of puncturing the blood vessel from such lateral movement. After the needle has been removed from the blood vessel, rearward movement of the holder 11 is continued until retainer 16 clears channel 29 so that support member 10 is entirely disassociated from stabilization member 20. Stabilization member 20 may then be pulled from the patient's skin without any effect upon the already removed needle.

Numerous modifications to the described embodiment may be employed without departing from the true spirit and and scope of the invention. For example, although protuberances 26 are desirable to increase the positive engagement between the stabilization member 20 and holder 11 during insertion as illustrated in FIGS. 3 and 4, such protuberances may be eliminated. Further, if desired, stabilization member 20 may be provided with two (2) additional wing-like members of the type described in the aforementioned U.S. patent application Ser. No. 99,926 so that initial stabilization may be enhanced upon insertion of the needle.

It should be noted that the generally rectangular cross-section for retainer 16 and slot 29 is not a limiting factor and can be replaced by triangular, trapezoidal, or other suitable configurations which serve to restrain transverse movement of the retainer relative to stabilization member 20 while permitting slidable longitudinal engagement between the channel and the retainer. Moreover, the slot for receiving retainer 16 need not be in the form of an open channel defined in bottom surface 22 of stabilization member 20. Instead, the slot may be defined through the rearward end of stabilization member 20 and surrounded on all sides. For such a slot, the retainer 16 would be received and entirely surrounded by the stabilization member 20.

The spacing between retainer 16 and holder 11 is selected relative to the thickness of stabilization member 20 so that the stabilization member can be firmly held in place in the U-shaped channel between retainer 16 and holder 11. The flexibility of retainer 16 aids in holding the stabilization member 20 in place. In any event, the engagement of stabilization member 20 between retainer 16 and holder 11 must not be so firm as to preclude smooth sliding of retainer 16 out of slot 29 at the time of withdrawal of needle 12 from the patient's blood vessel.

The slight convergence of retainer 16 toward holder 11 in the forward direction tends to raise the rearward end of holder 11, thereby tilting the forward end of holder 11 downward to present needle 12 at the proper angle for insertion into the patient's blood vessel.

It is desirable that the length of retainer 16 disposed in slot 29 be significantly greater than the length of needle 12 which is inserted into a patient's blood vessel. This feature retains the constraint by slot 29 against lateral movement by retainer 16 during withdrawal until the entire needle 12 has been removed.

As is noted from the foregoing description, the key features of the present invention are the firm gripping of holder member 11 by stabilization member 20 during insertion so that no relative movement between the two members is possible and the constraint of retainer 16 by slot 29 to preclude all but axial movement of holder 11 during stabilization and withdrawal.

While specific embodiments of the invention have been described and illustrated, it will be clear that variations of the details of the construction which are specifically illustrated and described, may be resorted to without departing from the true spirit and scope of the invention as defined in the appended claims.

I claim:

1. A fitting for use in performing a vascular puncture by a blood vessel-entering element and for positionally stabilizing the blood vessel-entering element in situ after the vascular puncture, said fitting comprising:
   a holder for said blood vessel-entering element, said holder including an elongate member having a longitudinal axis extending substantially parallel to said blood vessel-entering element;
   a stabilizing member having top and bottom surfaces, a longitudinally-extending support region on said first surface, and first and second wing-like members extending in opposite direction transversely from said support region, said stabilizing member being flexible about said support region to define a first flexed position in which parts of the wing-like members at said top surface are brought into contact, said wing-like members normally residing in substantially co-planar relation when said stabilizing member is in an unflexed second position;
   gripping means defined in said first position of said stabilizing member for securing said holder in contact with and extending along said support region to preclude all relative movement between said holder and said stabilizing member; and
   retaining means defined in said second position of said stabilizing member for retaining said holder in contact with and extending along said support region to preclude all relative movement between said holder and said stabilizing member except movement parallel to said longitudinal axis.

2. The fitting according to claim 1, wherein said retaining means comprises:
   a generally elongate retainer member having a proximal end secured to said holder and extending substantially longitudinally along and transversely spaced from said holder, said retainer member having a distal end spaced from said holder; and
   slot means defined in said stabilizing member and extending longitudinally beneath said support region for receiving said retainer member in longitudinally slidable engagement.

3. The fitting according to claim 2, wherein said retainer member has a prescribed cross-sectional configuration and wherein said slot means has a corresponding cross-sectional configuration for receiving said retainer member.

4. The fitting according to claim 2 or 3, wherein said slot means is defined as a channel in said bottom surface.

5. The fitting according to claim 4, wherein said channel has a predetermined depth and wherein said retainer member has a thickness substantially equal to said predetermined depth.

6. The fitting according to claim 1, 2, or 3, wherein said gripping means includes small protuberances extending from said top surface to said stabilizing member at said wing-like members to bear against said holder when said holder is positioned along said support region and said stabilizing means is in said first flexed position.

7. The fitting according to claim 3, wherein said prescribed cross-sectional configuration is rectangular.

8. The fitting according to claim 2, wherein said retainer member is flexible about said proximal end to permit resilient engagement of said stabilizing member between said retainer member and said holder member.

9. The fitting according to claim 2 or 3, wherein said slot means is defined as a channel in said bottom surface of said stabilizing member, and wherein the minimum spacing between said retainer member and said holder member is substantially the same as the thickness of said stabilizing member.

10. The fitting according to claim 1 or 3, wherein said retainer member is disposed at a slight angle relative to said holder member such that the distal end of said retainer member converges toward said longitudinal axis.

11. The fitting according to claim 1, 2, or 3, further comprising adhesive coating means disposed on portions of said bottom surface of said stabilizing member beneath said wings.

12. A fitting for use in inserting a blood vessel-entering element into a blood vessel and for positionally stabilizing the inserted element in situ, said fitting comprising:
   a holder for said element, said holder including an elongate section extending generally co-axially with said element, and a retainer section having a proximal end secured to said elongate section, a free distal end and a prescribed transverse cross-section, said retainer section extending substantially longitudinally alongside said elongate section in spaced relation therefrom except at said proximal end, the elongate section and retainer section having a predetermined minimum mutual spacing; and a stabilizing member having top and bottom surfaces and a support region extending along said top surface and adapted to support said holder, said stabilizing member being flexible about said support region to permit portions of the top surface to be brought toward one another to grip said holder in said support region, said stabilizing member having a slot defined therein extending longitudinally beneath said support region, said slot having a transverse cross-section corresponding to said prescribed transverse cross-section of said retainer section to permit said retainer section to be received for longitudinally slidable engagement in said slot, said bottom surface having an adhesive coating thereon at locations on opposite transverse sides of said support region.

13. The fitting according to claim 12, wherein said slot is defined as an open channel in the bottom surface of said stabilizing member, wherein the thickness of said stabilizing member from the depth of said slot to said top surface is substantially equal to said minimum mutual spacing to provide a friction-fit engagement of said stabilizing member between said elongate and retainer sections of said holder.

14. The fitting according to claim 13, wherein said retainer section converges slightly toward said elongate section toward said distal end such that said minimum mutual spacing occurs at said distal end.

15. The fitting according to claim 12 or 13, wherein said retainer means is flexible about its proximal end to provide resilient engagement of said stabilizing member between said retainer section and said elongate section.

16. A fitting for use in inserting a blood vessel-entering element into a blood vessel and for positionally stabilizing the inserted element in situ, said fitting comprising:

a holder for said element, said holder including a first section supporting said element, and a retainer section secured to said first section and having a free distal end and a prescribed transverse cross-section, said retainer section also having a portion which includes said distal end and which extends alongside said first section in spaced relation therefrom, the first section and retainer section having a predetermined minimum mutual spacing;

a stabilizing member having top and bottom surfaces and a support region extending along said top surface and adapted to support said holder, said stabilizing member being flexible about said support region to permit portions of the top surface to be brought toward one another to grip said holder in said support region, said stabilizing member having a slot defined in said bottom surface, said slot having a transverse cross-section corresponding to said prescribed transverse cross-section of said retainer section to permit said retainer section to be received in slidable engagement in said slot.

* * * * *